US012751905B2

(12) United States Patent
Zhou et al.

(10) Patent No.: US 12,751,905 B2
(45) Date of Patent: Oct. 6, 2026

(54) ANHYDROUS HAIR TREATMENT COMPOSITION COMPRISING MONO-ALCOHOLS AND FATTY COMPOUNDS

(71) Applicant: L'OREAL, Paris (FR)

(72) Inventors: XianZhi Zhou, Millburn, NJ (US); Sivaramakrishnan Muthukrishnan, Bridgewater, NJ (US)

(73) Assignee: L'OREAL, Paris (FR)

( * ) Notice: Subject to any disclaimer, the term of this patent is extended or adjusted under 35 U.S.C. 154(b) by 450 days.

(21) Appl. No.: 18/343,445

(22) Filed: Jun. 28, 2023

(65) Prior Publication Data

US 2025/0009618 A1 Jan. 9, 2025

(51) Int. Cl.

| | |
|---|---|
| ***A61K 8/34*** | (2006.01) |
| ***A61K 8/37*** | (2006.01) |
| ***A61Q 5/12*** | (2006.01) |

(52) U.S. Cl.

CPC .................. *A61K 8/34* (2013.01); *A61K 8/37* (2013.01); *A61Q 5/12* (2013.01); *A61K 2800/262* (2013.01); *A61K 2800/31* (2013.01); *A61K 2800/5922* (2013.01)

(58) Field of Classification Search

CPC ...... A61K 8/34; A61K 8/37; A61K 2800/262; A61Q 5/12

See application file for complete search history.

(56) References Cited

U.S. PATENT DOCUMENTS

| | | | |
|---|---|---|---|
| 8,563,016 | B2 | 10/2013 | Agarelli et al. |
| 11,058,618 | B1 | 7/2021 | Liang |
| 11,337,906 | B2 | 5/2022 | Lee et al. |
| 2021/0369579 | A1 | 12/2021 | Liang et al. |
| 2022/0202674 | A1 | 6/2022 | Zhou et al. |
| 2022/0202686 | A1 | 6/2022 | Zhou et al. |

FOREIGN PATENT DOCUMENTS

| | | | | |
|---|---|---|---|---|
| FR | 3104959 | A1 | 6/2021 | |
| FR | 3109727 | A1 | 8/2022 | |
| FR | 3124949 | A1 | 1/2023 | |
| FR | 3120192 | A1 | 4/2024 | |
| KR | 20130046109 | A | 5/2013 | |
| KR | 101774460 | B1 | 9/2017 | |
| WO | 03037280 | A1 | 5/2003 | |
| WO | WO-2020183362 | A1 * | 9/2020 | ............. A61K 8/922 |
| WO | 2023280485 | A1 | 1/2023 | |

OTHER PUBLICATIONS

WO 2023280485 A1, ip.com translation (Year: 2023).*

FR 3124949 A1, translation from ip.com (Year: 2023).*

Byrdie, We Had No Idea This Is How Hair Dye Is Made by K. Mclintock. 2021. https://www.byrdie.com/hair-dye-ingredients (Year: 2021).*

Healthline, Shampoo Ingredients for Different Hair Needs: What to Look for by M. Vinall. 2020. https://www.healthline.com/health/shampoo-ingredients-for-different-hair-needs (Year: 2020).*

Uplift, Hair Products 101: Understanding Ingredients and Labels. 2023. https://upliftprovisionsco.com/blogs/news/hair-products-101-understanding-ingredients-and-labels?srsltid=AfmBOorSo3SncJPbdDYCFp11RlazQxanauBUe-xzKe5qnINSIBWpAPof (Year: 2023).*

Preliminary Search Report and Written Opinion issued on May 16, 2024, for corresponding French Application No. FR 2309255.

* cited by examiner

*Primary Examiner* — Sue X Liu
*Assistant Examiner* — Susannah S Armstrong
(74) *Attorney, Agent, or Firm* — POLSINELLI PC

(57) ABSTRACT

The instant disclosure is drawn to an essentially anhydrous hair treatment composition; and to methods for conditioning, managing, and improving the look and feel of hair. The compositions include: (a) one or more linear or branched monoalcohols having from 2 to 8 carbon atoms; (b) one or more fatty alcohols; (c) one or more fatty compounds; and (d) about 1 to about 12 wt. % of one or more cationic surfactants; wherein (a) is in an amount greater than (b). The composition is typically transparent or translucent, forms a lamellar phase in situ when contacted with water, and provides deep conditioning and other benefits to the hair.

11 Claims, 1 Drawing Sheet

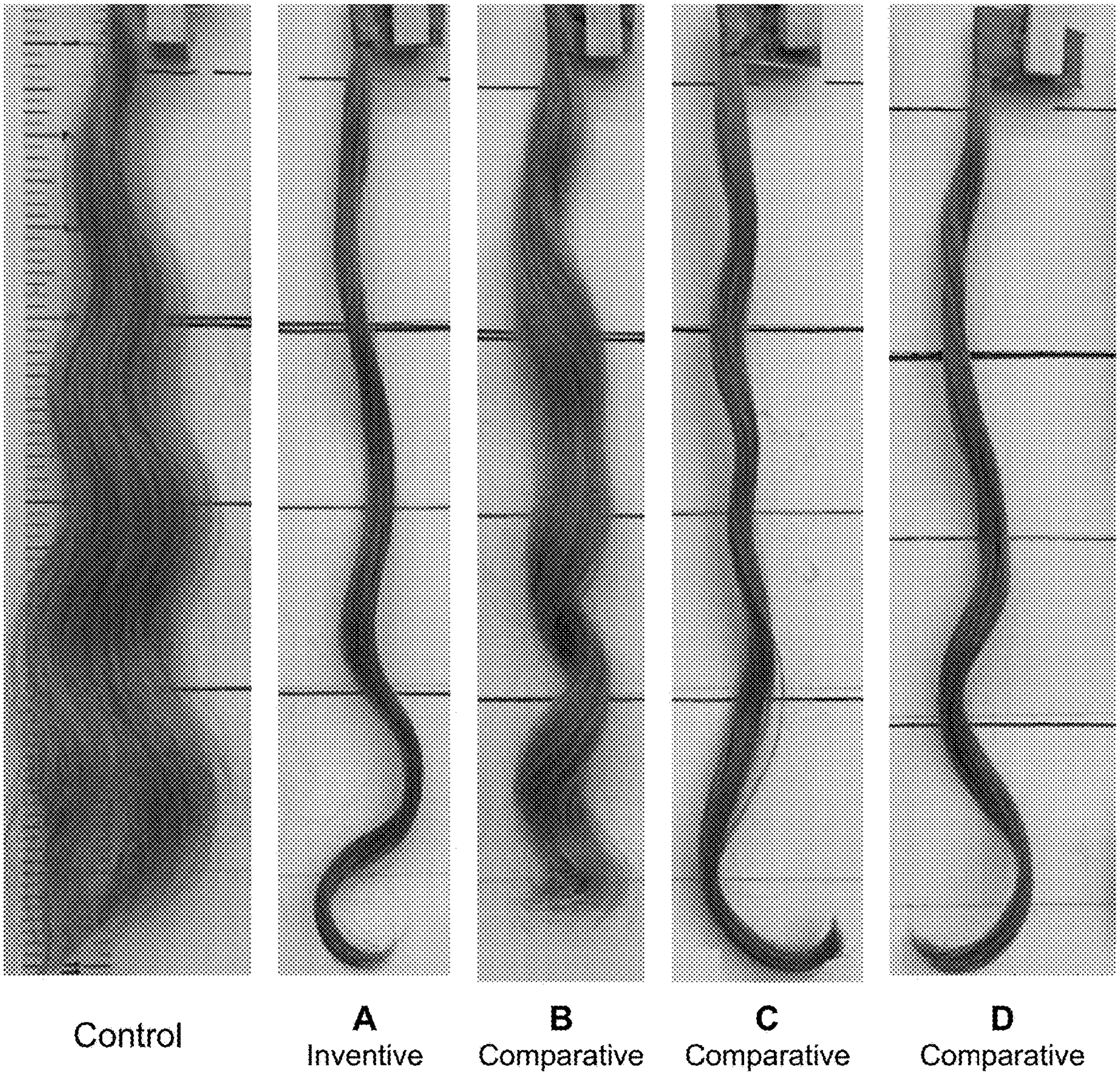
Control
A
Inventive
B
Comparative
C
Comparative
D
Comparative

ANHYDROUS HAIR TREATMENT COMPOSITION COMPRISING MONO-ALCOHOLS AND FATTY COMPOUNDS

FIELD OF THE DISCLOSURE

The instant disclosure is drawn to hair treatment compositions containing one or more monoalcohols and fatty compounds; and to methods for treating hair, for example, conditioning, managing, and improving the look and feel of hair.

BACKGROUND

Many individuals suffer from dry and damaged hair. Dryness and damage can occur due to several factors including weather exposure, mechanical treatments (e.g., brushing hair), excessive treatments using chemicals, dying hair, heat styling, etc. In combination, using cleansing products that can be excessively stripping of hair's natural oils can also not only lead to split ends and dull hair, but also exacerbate dry hair. To mitigate the damage, oil treatments, conditioner, hair masks, and chemical treatments are commonly used.

The popularity and usage of oils for dry hair treatments has increased due to their effectiveness and simplicity. Commonly used oils include olive oil, mineral oil, avocado oil, apricot kernel oil, rice bran oil, and coconut oil. However, one problem is that effects are not usually seen after more than several hours (e.g., 8 hours) of treatment and several treatments are usually required, making it time consuming and labor intensive.

Individuals desire a treatment for hair or damaged hair that is not time consuming and labor intensive to use. A variety of approaches have been developed to condition the hair. A common method of providing conditioning benefit is through using conditioning agents such as cationic surfactants and polymers, high melting point fatty compounds, low melting point oils, silicone compounds, and combinations thereof. Most of these conditioning agents are known to provide various conditioning benefits.

However, there is still a need for providing improved hair manageability, for example, improved hair alignment, reduced unwanted volume (especially reduced frizz), and increased shine. There is also a need to develop hair care products that can impart other benefits at the same time in addition to caring and conditioning benefits, such as styling, volume, shaping, curl definition (for curly or wavy hair), and restyle-ability or reshaping (without the need to reapply the product).

BRIEF DESCRIPTION OF THE FIGURES

Implementation of the present technology is described, by way of example only, with reference to the attached FIGURE, wherein:

THE FIGURE shows a swatch treated with a hair treatment composition according to the instant disclosure, hair swatches treated with comparative compositions, and a hair swatch serving as a control.

SUMMARY OF THE DISCLOSURE

The instant disclosure is drawn to an essentially anhydrous hair treatment composition, and to methods for conditioning, managing, and improving the look and feel of hair. The compositions are useful in methods for treating hair, for example, conditioning, softening, and reducing the frizz of hair. The compositions are unique because they include large proportions of fatty compounds and monoalcohols having from 2 to 8 carbon atoms, such as ethanol. The compositions are typically solubilized, clear (transparent), and free flowing. Upon application to wet or damp hair, or dilution with water, the composition interacts with the available water and forms a lamellar phase in situ, which enhances the composition's moisturizing and conditioning ability. The anhydrous composition typically includes:

(a) one or more monoalcohols having from 2 to 8 carbon atoms;
(b) one or more fatty alcohols;
wherein (a) is in an amount equal to or greater than (b);
(c) one or more fatty compounds other than the one or more fatty alcohols of (b); and
(d) one or more cationic surfactants.

The hair treatment compositions do not require glycols having from 2 to 10 carbon atoms, such as propylene glycol. In various embodiments, the hair treatment compositions are free or essentially free from propylene glycol. In further embodiments, the hair treatment compositions are free or essentially free from glycols having from 2 to 10 carbon atoms. In yet another embodiment, the composition is free or essentially free from polyols having from 2 to 10 carbons.

As mentioned above, the composition is typically a solubilized, non-emulsified composition that is transparent or translucent, preferably transparent. Upon application to wet or damp hair, or upon dilution with water, the composition forms a lamellar phase in situ to provide deep moisturizing and conditioning benefits to the hair. Available water on the wet or damp hair interacts with the composition prompting formation of a lamellar phase. Additional water can be used to enhance formation of the lamellar phase, for example, when the hair is not very wet.

The monoalcohols having from 2 to 8 carbon atoms may be linear or branched. Nonlimiting examples of such monoalcohols include ethanol, propanol, butanol, pentanol, hexanol, isopropyl alcohol, cyclohexanol, isobutyl alcohol, 2-methyl-2-butanol (2-methylbutan-2-ol), or combinations thereof.

The one or more fatty alcohol may be selected from saturated or unsaturated, linear or branched fatty alcohols having from 10 to 30 carbon atoms, preferably from 12 to 28 carbon atoms, more preferably from 14 to 24 carbon atoms. Nonlimiting examples of fatty alcohols include decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a combination thereof. In some instances, the cosmetic compositions preferably include cetyl alcohol, behenyl alcohol, cetearyl alcohol, or a combination thereof.

Nonlimiting examples of fatty compounds include hydrocarbons, hydrocarbons containing more than 16 carbon atoms, oils or animal origin, oil of plant origin, hydrocarbon-based oils, synthetic triglycerides, fluoro oils, non-salified fatty acids, fatty acid and/or fatty alcohol esters, fatty acids, waxes, and combinations thereof. For purposes of the instant disclosure, "fatty alcohols" are set forth separately and considered a different component than the one or more fatty compounds, although fatty alcohols are fatty compounds. In various embodiments, preferred fatty compounds are selected from fatty esters, fatty ethers, propylene glycol fatty esters, fatty carbonate esters, or a combination thereof, in particular, propylene glycol fatty acid esters such as propylene glycol monolaurate, propylene glycol ricinoleate, propylene glycol monooleate, propylene glycol monocaprylate, propylene glycol dicaprylate/dicaprate, propylene glycol dioctanoate, or a combination thereof.

In various embodiments, at least one of the one or more fatty compounds is a polar fatty compound. Nonlimiting examples of polar fatty compounds include dibutyl adipate, propylene glycol dicaprylate, propylene glycol dicaprylate/dicaprate, C12-15 alkylbenzoate, propylheptyl caprylate, ethylhexyl palmitate, coco-caprylate/caprate, isotridecyl isononanoate, diisopropyl sebacate, cetearyl isononanoate, isopropyl palmitate, butyloctylsalicylate, butylene glycol dicaprylate/dicaprate, diisopropyl adipate, isononyl isononanoate, diethyl sebacate, diisopropyl dilinoleate, ethyl oleate, ethylhexyl hydroxystearate, glycol distearate, glycol stearate, hydroxyoctacosanyl hydroxystearate, isopropyl isostearate, isopropyl myristate, isopropyl palmitate, isopropyl stearate, methyl glucose sesquistearate, methyl laurate, methyl salicylate, methyl stearate, myristyl lactate, octyl salicylate, oleyl oleate, PPG-20 methyl glucose ether distearate, propylene glycol diacetate, propylene glycol dicaprylate, propylene glycol monolaurate, propylene glycol monopalmitostearate, propylene glycol ricinoleate, triacetin and sucrose distearate, or combinations thereof.

Nonlimiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and combinations thereof.

In various embodiments, at least one of the one or more cationic surfactants is an amidoamine surfactants. Nonlimiting examples of amidoamine surfactants include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, stearamidoethyldiethylamine, or a combination thereof.

The compositions can be applied on wet or damp hair or be diluted and applied on dry or wet hair. It can be applied immediately after shampooing the hair, for example, in place of a conditioner. The compositions can also be applied on hair immediately after shampooing and conditioning the hair, for example, as a mask rinse-off or leave-in treatment. The compositions may even be applied before shampooing the hair as a pre-treatment composition. In various embodiments, after the compositions are applied to the hair, the hair is rinsed with water, dried, and styled as desired. In other embodiments, the compositions are applied as a leave-on product. For example, the compositions can be diluted with water and applied to hair and allowed to remain on the hair indefinitely, i.e., the hair composition is not removed or rinsed from the hair prior to styling the hair.

DETAILED DESCRIPTION OF THE DISCLOSURE

The hair treatment compositions of the instant disclosure are particularly useful for treating hair, for example, conditioning, managing, and improving the look and feel of hair. Due to their unique ingredients and properties, the compositions enhance the deposition of conditioning active agents such as cationic surfactants and fatty compounds including fatty alcohol onto/into the hair to provide moisturization and conditioning properties. On the other hand, treatment with the composition does not leave the hair "too greasy" or "weighed down." Thus, the hair treatment composition imparts a natural, softness, shine, and moisturized feel to the hair while simultaneously improving body, shine, and manageability. The compositions typically include:

(a) about 1 to about 20 wt. % of one or more linear or branched monoalcohols having from 2 to 8 carbon atoms;

(b) about 2 to about 15 wt. % of one or more fatty alcohols;

wherein (a) is in an amount greater than (b);

(c) about 50 to about 90 wt. % of one or more fatty compounds;

(d) about 1 to about 12 wt. % of one or more cationic surfactants;

wherein the composition is essentially free from propylene glycol; and all percentages by weight are based on a total weight of the composition.

The composition is typically a solubilized, non-emulsified composition. In various embodiments, the composition is transparent or translucent. Upon application to wet or damp hair or dilution with water then application onto hair, the composition preferably forms a lamellar phase in situ. In other embodiments, upon contact with water, the composition preferably forms an opaque appearance. When the hair treatment composition is applied and massaged into hair, it interacts with the water and becomes luscious. The composition can enhance the deposition of conditioning active agents such as cationic surfactants and fatty compounds including fatty alcohol onto/into the hair to provide moisturization and conditioning properties. On the other hand, treatment with the composition does not leave the hair "too greasy" or "weighed down." Thus, the hair treatment composition imparts a natural, softness, shine, and moisturized feel to the hair while simultaneously improving body, shine, and manageability.

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure.

The term "translucent" with respect to a translucent composition indicates that the composition has a transmittance of at least 50% at a wavelength of 600 nm, for example measured using a Lambda 40 UV-visible spectrometer.

The term "opaque" with respect to an opaque composition indicates the composition is not transparent or translucent, i.e., has a transmittance of less than 50% at a wavelength of 600 nm, for example measured using a Lambda 40 UV-visible spectrometer.

(a) Monoalcohols Having from 2 to 8 Carbon Atoms

The compositions include one or more monoalcohols having from 2 to 8 carbon atoms. Nonlimiting examples include ethanol, propanol, butanol, pentanol, hexanol, isopropyl alcohol, cyclohexanol, isobutyl alcohol, 2-methyl-2-butanol (2-methylbutan-2-ol), or combinations thereof. In a preferred embodiment, at least one of the one or more monoalcohols is ethanol.

The total amount of the one or more monoalcohols having from 2 to 8 carbon atoms will vary. Nonetheless, in various embodiments, the hair treatment composition includes about 3 to about 30 wt. % of the one or more monoalcohols having from 2 to 8 carbon atoms, based on a total weight of the hair treatment composition. In further embodiments, the hair treatment composition includes about 3 to about 25 wt. %, about 3 to about 20 wt. %, about 3 to about 18 wt. %, about 3 to about 15 wt. %, about 3 to about 12 wt. %, about 5 to about 30 wt. %, about 5 to about 25 wt. %, about 5 to about 20 wt. %, about 5 to about 18 wt. %, about 5 to about 15 wt. %, about 5 to about 12 wt. %, about 8 to about 30 wt. %, about 8 to about 25 wt. %, about 8 to about 20 wt. %, about 8 to about 18 wt. %, about 8 to about 15 wt. %, or about 8 to about 12 wt. % of the one or more monoalcohols having from 2 to 8 carbon atoms, based on the total weight of the hair treatment composition.

(b) Fatty Alcohols

The term "fatty alcohol" means an alcohol comprising at least one hydroxyl group (OH), and typically comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In various embodiments, the compositions include at least one solid fatty alcohol. Solid fatty alcohols are fatty alcohols that are solid at ambient temperature and at atmospheric pressure (25° C., 780 mmHg), and are insoluble in water, i.e., they have a water solubility of less than 1% by weight, preferably less than 0.5% by weight, at 25° C., 1 atm. The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms. Nonlimiting examples include lauryl alcohol (1-dodecanol); myristyl alcohol (1-tetradecanol), cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol), myricylic alcohol (1-triacontanol), and combinations thereof. In a preferred embodiment, the compositions include at least one solid fatty alcohol selected from myristyl alcohol, cetyl alcohol, stearyl alcohol, behenyl alcohol and combinations thereof such as cetylstearyl or cetearyl alcohol.

In various embodiments, the compositions include at least one liquid fatty alcohol, in particular containing C10-C34 and preferably have branched carbon chains and/or have one or more, preferably 1 to 3 double bonds. They are preferably branched and/or unsaturated (C═C double bond) and contain from 12 to 40 carbon atoms. The liquid fatty alcohols may be represented by: R—OH, wherein R denotes a C12-C24 branched or straight alkyl group or an alkenyl group, R being optionally substituted by one or more hydroxy groups. In certain embodiments, the liquid fatty alcohols are selected from branched saturated alcohols. Preferably, R does not contain a hydroxyl group. Nonlimiting examples include oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and combinations thereof. In other embodiments, the compositions are free or essentially free from liquid fatty alcohols, including the liquid fatty alcohols referenced above.

In a preferred embodiment, the one or more fatty alcohols are linear (straight chain) saturated fatty alcohols having from 10 to 30 carbon atoms, preferably from 12 to 28 carbon atoms, more preferably from 14 to 24 carbon atoms. Nonlimiting examples include decyl alcohol, undecyl alcohol, dodecyl alcohol, myristyl alcohol, cetyl alcohol, stearyl alcohol, cetearyl alcohol, behenyl alcohol, myricyl alcohol and a combination thereof.

The total amount of the one or more fatty alcohols in the hair treatment composition will vary. Nonetheless, in various embodiments, the total amount of the one or more fatty alcohols is from about 1 to about 15 wt. %, preferably about 2 to about 15 wt. %, based on the total weight of the composition. In further embodiments, the hair treatment composition includes about 2 to about 12 wt. %, about 2 to about 10 wt. %, about 2 to about 8 wt. %, about 3 to about 15 wt. %, about 3 to about 12 wt. %, about 3 to about 10 wt. %, about 3 to about 8 wt. %, or about 4 to about 6 wt. % of the one or more fatty alcohols, based on a total weight of the hair treatment composition.

Ratio of (a) to (b)

The amount of the one or more monoalcohols having from 2 to 8 carbon atoms of (a) is typically greater than the amount of the one or more fatty alcohols of (b). For example, in various embodiments, the weight ratio of (a) to (b) is from about 1:1 to about 10:1 ((a):(b)). In further embodiments, the weight ratio of (a) to (b) is from about 1.1:1 to about 1:1, about 1.1:1 to about 8:1, from about 1.1:1 to about 5:1, from about 1.1:1 to about 4:1, from about 1.1:1 to about 3:1, from about 1.3:1 to about 8:1, from about 1.3:1 to about 5:1, from about 1.3:1 to about 4:1, from about 1.3:1 to about 3:1, from about 1.5:1 to about 8:1, from about 1.5:1 to about 5:1, from about 1.5:1 to about 4:1, from about 1.5:1 to about 3:1, from about 1.8:1 to about 8:1, from about 1.8:1 to about 5:1, from about 1.8:1 to about 4:1, from about 1.8:1 to about 3:1.

(c) Fatty Compounds Other than Fatty Alcohols

In various embodiments, the compositions of the instant disclosure include one or more fatty compounds other than the fatty alcohols. Nonlimiting examples of fatty compounds include oils, mineral oil, fatty acids, fatty alcohol derivatives, fatty acid derivatives (such as alkoxylated fatty acids or polyethylene glycol esters of fatty acids, or propylene glycol esters of fatty acids, or butylene glycol esters of fatty acids, or esters of neopentyl glycol and fatty acids, or polyglycerol/glycerol esters of fatty acids, or glycol diesters, or diesters of ethylene glycol and fatty acids, or esters of fatty acids and fatty alcohols, or esters of short chain alcohols and fatty acids), esters of fatty alcohols, hydroxy-substituted fatty acids, waxes, triglyceride compounds, lanolin, diethylhexyl maleate, fatty carbonate, and a combination thereof. Non-limiting examples of fatty acids, fatty alcohol derivatives, and fatty acid derivatives are found in International Cosmetic Ingredient Dictionary, Sixteenth Edition, 2016, which is incorporated by reference herein in its entirety.

In various embodiments, the one or more fatty compounds other than the fatty alcohols of (b) include one or more liquid fatty compounds, also referred to "oils." "Oil" is used herein to refer to an organic compound other than the fatty alcohols of (b) that is insoluble in water at normal temperature (25° C.) and at atmospheric pressure (760 mmHg), i.e. it has a water solubility of less than 5% by weight, or less than 1% by weight, or less than 0.1% by weight. Oils have in their structure at least one hydrocarbon chain having at least 6 carbon atoms. Furthermore, oils are generally soluble in organic solvents in the same conditions of temperature and pressure, for example in chloroform, ethanol, benzene or decamethylcyclopentasiloxane. Furthermore, oils are liquid at ordinary temperature (25° C.) and at atmospheric pressure (760 mmHg).

Fatty alcohol derivatives include alkyl ethers of fatty alcohols, alkoxylated fatty alcohols, alkyl ethers of alkoxylated fatty alcohols, esters of fatty alcohols and a combination thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a combination thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a combination thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a combination thereof. Preferred for use herein are glycerol monostearate, 12-hydroxy stearic acid, and a combination thereof. Fatty carbonates include dialkyl carbonates. Non-limiting examples of dialkyl carbonates include those of the following formula: $R_1O(C{=}O)OR_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, for example, C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a combination thereof. In some instances, it is preferable to include one or more dialkyl carbonates, in particular dicaprylyl carbonate.

In some cases, the one or more fatty compounds include one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compounds may be selected from fatty acids, fatty alcohol derivatives, fatty acid derivatives, and combinations thereof. Nonlimiting examples of the high melting point compounds are found in the International Cosmetic Ingredient Dictionary, Sixteenth Edition, 2016, which is incorporated by reference herein in its entirety.

In some instances, fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a combination thereof.

Mention may be made, among the waxes capable of being used as fatty compounds, of animal waxes, such as beeswax, vegetable waxes, such as sunflower seed (*Helianthus annuus*), carnauba, candelilla, ouricury or Japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In a preferred embodiment, the one or more fatty compounds other than the one or more fatty alcohols of (b) are selected from polar fatty compounds containing at least one ester group. Nonlimiting examples include dibutyl adipate, propylene glycol dicaprylate, propylene glycol dicaprylate/dicaprate, dicaprylyl carbonate, dicaprylyl ether, diethylhexyl maleate, C12-15 alkylbenzoate, propylheptyl caprylate, ethylhexyl palmitate, coco-caprylate/caprate, isotridecyl isononanoate, diisopropyl sebacate, cetearyl isononanoate, isopropyl palmitate, butyloctylsalicylate, butylene glycol dicaprylate/dicaprate, diisopropyl adipate, isononyl isononanoate, diethyl sebacate, diisopropyl dilinoleate, ethyl oleate, ethylhexyl hydroxystearate, glycol distearate, glycol stearate, hydroxyoctacosanyl hydroxystearate, isopropyl isostearate, isopropyl myristate, isopropyl palmitate, isopropyl stearate, methyl glucose sesquistearate, methyl laurate, methyl salicylate, methyl stearate, myristyl lactate, octyl salicylate, oleyl oleate, PPG- 20 methyl glucose ether distearate, propylene glycol diacetate, propylene glycol dicaprylate, propylene glycol monolaurate, propylene glycol monopalmitostearate, propylene glycol ricinoleate, triacetin and sucrose distearate, or combinations thereof.

In a preferred embodiment, the one or more non-fatty compounds other than fatty alcohols are polar fatty compounds selected from propylene glycol fatty acid esters. Nonlimiting examples include propylene glycol monolaurate, propylene glycol ricinoleate, propylene glycol monooleate, propylene glycol monocaprylate, propylene glycol dicaprylate/dicaprate, or propylene glycol dioctanoate, wherein propylene glycol dicaprylate/dicaprate, is particularly preferred.

In a preferred embodiment, the one or more fatty compounds are selected from fatty esters, fatty ethers, propylene glycol fatty esters, fatty carbonate esters, oils, and fatty acids. Nonlimiting examples of these types of fatty compounds are set forth below.

i. Fatty Esters

Non-limiting examples of fatty esters include fatty esters from a $C_6$-$C_{32}$ fatty acid and/or a $C_6$-$C_{32}$ fatty alcohol. These esters may be esters of saturated or unsaturated, linear or branched $C_1$-$C_{26}$ aliphatic mono or polyacids and of saturated or unsaturated, linear or branched $C_1$-$C_{26}$ aliphatic mono or polyalcohols, the total number of carbon atoms in the esters being greater than or equal to 10. In some cases, for the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate, glyceryl oleate, and isostearyl neopentanoate.

In various embodiments, the compositions of the instant disclosure may include cetyl esters. Cetyl esters is a mixture of the following esters of saturated fatty acids and fatty alcohols: cetyl palmitate, cetyl stearate, myristyl myristate, myristyl stearate, cetyl myristate, and stearyl stearate.

Mention is made of esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate, diisopropyl sebacate, diisopropyl adipate, di-n-propyl adipate, triisopropyl citrate, glyceryl trilactate, glyceryl trioctanoate, neopentyl glycol diheptanoate, and diethylene glycol diisononanoate.

Nonlimiting examples of liquid esters (ester oils) or liquid fatty esters that may be mentioned include, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, camelina oil, tamanu oil, babassu oil and pracaxi oil, jojoba oil, and shea butter oil, and caprylic/capric triglyceride.

Nonlimiting examples of solid fatty esters include solid esters obtained from $C_9$-$C_{26}$ fatty acids and from $C_9$-$C_{26}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

ii. Fatty Ethers

Nonlimiting examples of fatty ether include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a combination thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and combinations thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and combinations thereof. In yet another embodiment, at least one of the emollients is a fatty ether selected from stearyl ether, dicaprylyl ether, dicetyl ether, distearyl ether, dodecyl ether, dilauryl ether, dimyristyl ether, diisononyl ether, or a combination thereof.

In a preferred embodiment, the composition includes dicaprylyl ether, and optionally one or more additional emollients.

iii. Propylene Glycol Fatty Acid Esters

Nonlimiting examples of propylene glycol fatty acid esters include propylene glycol esters of medium chain fatty acids (fatty acids having from 6 to 12 carbon atoms), such as propylene glycol dicaprylate/dicaprate, propylene glycol dipelargonate, and propylene glycol dilaurate. A preferred propylene glycol fatty acid ester is propylene glycol dicaprylate/dicaprate. The term "propylene glycol dicaprylate/dicaprate" is understood by those in the art to refer to a combination containing propylene glycol dicaprylate, propylene glycol dicaprylate-caprate, and propylene glycol dicaprate, which may vary in the ratio of these components. An example of a commercially available form of propylene glycol dicaprylate/dicaprate is "CAPTEX® 200," available from the Abitec Corp. (Columbus, OH, USA). Additional nonlimiting examples of propylene glycol fatty acid esters include propylene glycol monolaurate, propylene glycol ricinoleate, propylene glycol monooleate, propylene glycol monocaprylate, propylene glycol dicaprylate/dicaprate, or propylene glycol dioctanoate, wherein propylene glycol dicaprylate/dicaprate, is particularly preferred.

iv. Fatty Carbonate

Nonlimiting examples of fatty carbonates include dialkyl carbonates of formula: $R_1O(C{=}O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a combination thereof.

V. Oils

Nonlimiting examples of oils include hydrocarbons, triglyceride oils of plant, animal or synthetic origin. Nonlimiting examples of hydrocarbons include linear or branched, optionally cyclic C6-C16 alkanes; hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane. Non-limiting examples of triglyceride oils of plant, animal or synthetic origin include liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, camelina oil, tamanu oil, babassu oil and pracaxi oil, jojoba oil, perhydrosqualene, arara oil and shea butter oil.

vi. Fatty Acids

In various embodiments, the compositions of the instant disclosure include one or more fatty acids. However, in other embodiments, the compositions do not include fatty acids, i.e., the compositions are free or essentially free from fatty acids. A fatty acid is a carboxylic acid with an aliphatic chain, for example, of 8 to 30 carbon atoms, preferably 8 to 28 carbon atoms, more preferably from 12 to 26 carbon atoms, which is either saturated or unsaturated, and branched or unbranched. Most naturally occurring fatty acids have an unbranched chain of an even number of carbon atoms, from 6 to 28. In some instances, naturally occurring fatty acids are preferred.

Nonlimiting examples of fatty acids include caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, isostearic acid, and a combination thereof.

vii. Silicone Oils

In various embodiments, the compositions of the instant disclosure include one or more silicone oils.

Nonlimiting examples of silicone oils include dimethicone, dimethiconol, cyclomethicone, polysilicone-11, phenyl trimethicone, trimethylsilylamodimethicone, and stearoxytrimethylsilane. In a preferred embodiment, the one or more silicones are non-volatile silicone oils. Useful silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes or 2-phenylethyl) trimethylsiloxysilicates. Other examples of silicone oils that may be mentioned include volatile linear or cyclic silicones, such as those with a viscosity 8 centistokes and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or combinations thereof. In various embodiments, the hair treatment compositions include one or more silicone oils chosen from dimethicone, dimethiconol, cyclomethicone, polysilicone-11, phenyl trimethicone, and amodimethicone, and a combination thereof.

The total amount of the one or more fatty compounds other than fatty alcohols will vary. Nonetheless, in various embodiments, the hair treatment composition includes about 50 to about 90 wt. % of one or more fatty compounds other than the fatty alcohols, based on a total weight of the hair treatment composition. In further embodiments, the hair treatment composition includes about 55 to about 90 wt. %, about 60 to about 90 wt. %, about 65 to about 90 wt. %, about 70 to about 90 wt. %, about 50 to about 85 wt. %, about 55 to about 85 wt. %, about 60 to about 85 wt. %, about 65 to about 85 wt. %, about 70 to about 85 wt. %, about 50 to about 82 wt. %, about 55 to about 82 wt. %, about 60 to about 82 wt. %, about 65 to about 82 wt. %, about 70 to about 82 wt. %, about 50 to about 80 wt. %, about 55 to about 80 wt. %, about 60 to about 80 wt. %, about 65 to about 80 wt. %, or about 70 to about 80 wt. % of the one or more fatty compounds other than fatty alcohols.

(d) Cationic Surfactants

The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and a combination thereof.

In various embodiments, the one or more cationic surfactants are preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, and a combination thereof.

In further embodiments, the one or more cationic surfactants are preferably selected from cetrimonium chloride, behentrimonium chloride, behentrimonium methosulfate, stearamidopropyl dimethylamine, and a combination thereof.

In a preferred embodiment, at least one of the one or more cationic surfactants include one or more amidoamine surfactants. Nonlimiting examples of amidoamine surfactants include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, stearamidoethyldiethylamine, or a combination thereof.

A more exhaustive but non-limiting list of cationic surfactants that may be included in the hair treatment compositions is provided later, under the heading "Additional Cationic Surfactants," which is incorporated herein by reference.

The total amount of the one or more cationic surfactants in the composition will vary. Nonetheless, in various embodiments, the hair treatment composition includes about 0.5 to about 12 wt. % of one or more cationic surfactants, based on a total weight of the hair treatment composition. In further embodiments, the hair treatment composition includes about 0.5 to about 10 wt. %, about 0.5 to about 8 wt. %, about 0.5 to about 5 wt. %, about 0.5 to about 3 wt. %, about 1 to about 12 wt. %, about 1 to about 10 wt. %, about 1 to about 8 wt. %, about 1 to about 5 wt. %, about 1 to about 3 wt. %, about 2 to about 12 wt. %, about 2 to about 10 wt. %, about 2 to about 8 wt. %, about 2 to about 6 wt. %, about 2 to about 5 wt. %, or about 2 to about 4 wt. % of the one or more cationic surfactants, based on a total weight of the hair treatment composition.

(e) Miscellaneous Ingredients

The compositions the instant disclosure may optionally include (or optionally exclude) one more miscellaneous ingredients. Miscellaneous ingredients are ingredients that are compatible with the hair treatment compositions and do not disrupt or materially affect the basic and novel properties of the compositions. Nonlimiting examples of miscellaneous ingredients include preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

In various embodiments, the compositions of the instant disclosure include one or more miscellaneous ingredients selected from preservatives, fragrances, pH adjusters, salts, chelating agents, buffers, composition colorants, fillers (such as talc, calcium carbonate, silica, including hydrated silica), vitamins, botanical extracts, and a combination thereof. For example, the compositions may include silica (or hydrated silica), tocopherol, fragrances, or a combination thereof.

In the context of the instant disclosure, a "composition colorant" is a compound that colors the composition but does not have an appreciable coloring effect on hair. In other words, the composition colorant is included to provide a color to the composition for aesthetic appeal but is not intended to impart coloring properties to hair. As an example, hair styling gels, can be found in a variety of different colors (e.g., light blue, light pink, etc.) yet application of the styling gel to hair does not visibly change the color of the hair.

The total amount of the one or more miscellaneous ingredients, if present, will vary. Nonetheless, in various embodiments, the compositions of the instant disclosure include from about 0.001 to about 10 wt. % of one or more miscellaneous ingredients, based on the total weight of the composition. In further embodiments, the compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the hair treatment composition.

Water and Polyols

The hair treatment compositions of the instant disclosure include little, if any, water and propylene glycol. Preferably, the hair treatment compositions are free or essentially free from water and propylene glycol. Nonetheless, in various embodiments, the hair treatment composition includes less than 10 wt. % of water and propylene glycol, based on the total weight of the hair treatment composition. In some instances, the hair treatment composition includes less than 8 wt. %, less than 6 wt. %, less than 4 wt. %, less than 2 wt. %, less than 0.5 wt. %, or less than 0.1 wt. % of water and propylene glycol, based on the total weight of the hair treatment composition.

Water, if present, may be in an amount less than 10 wt. %, based on the total weight of the hair treatment composition. Preferably, the amount of water, if present, is in an amount less than 8 wt. %, less than 6 wt. %, less than 4 wt. %, less than 2 wt. %, about 0.5 wt. %, or less than 0.1 wt. %, based on a total weight of the hair treatment compositions. Furthermore, the hair treatment compositions may include from about 0.01 to about 4 wt. %, about 0.01 to about 3 wt. %, about 0.01 to about 2 wt. %, about 0.01 to about 1 wt. %, about 0.01 to about 0.5 wt. %, about 0.01 to about 0.1 wt. % of water, based on the total weight of the hair treatment composition.

Propylene glycol, if present, is in an amount less than 10 wt. %, based on a total weight of the hair treatment composition. Preferably, the amount of propylene glycol, if present, is an amount less than 8 wt. %, less than 6 wt. %, less than 4 wt. %, less than 2 wt. %, about 0.5 wt. %, or less than 0.1 wt. %, based on the total weight of the hair treatment compositions. Furthermore, the hair treatment composition may include from about 0.01 to about 4 wt. %, about 0.01 to about 3 wt. %, about 0.01 to about 2 wt. %, about 0.01 to about 1 wt. %, about 0.01 to about 0.5 wt. %, about 0.01 to about 0.1 wt. % of propylene glycol, based on the total weight of the hair treatment composition.

In further embodiments, the hair treatment composition is free or essentially free from glycols having from 2 to 10 carbon atoms. Nonlimiting examples of glycols having from 2 to 10 carbon atoms include ethylene glycol, propylene glycol, butylene glycol, hexylene glycol, pentylene glycol, diethylene glycol, dipropylene glycol, 1,3 propanediol, or a combination thereof. Preferably, the amount of the glycols having from 2 to 10 carbon atoms, if present, is an amount less than 10 wt. %, less than 8 wt. %, less than 6 wt. %, less than 4 wt. %, less than 2 wt. %, less than 0.5 wt. %, or less than 0.1 wt. %, based on the total weight of the hair treatment composition. Furthermore, in certain embodiments, the hair treatment composition may include from about 0.01 to about 4 wt. %, about 0.01 to about 3 wt. %, about 0.01 to about 2 wt. %, about 0.01 to about 1 wt. %, about 0.01 to about 0.5 wt. %, about 0.01 to about 0.1 wt. % of glycols having from 2 to 10 carbon atoms, based on the total weight of the hair treatment composition.

In various embodiments, the compositions of the instant disclosure may optionally include one or more of polyethylene glycols (PEG), anionic surfactants, nonionic surfactants, anionic polymers, or combinations thereof. In other embodiments, the compositions of the instant disclosure are free or essentially free from one or more of polyethylene glycols (PEG), nonionic surfactants, anionic surfactants, anionic polymers, or combinations thereof.

In certain embodiments, the compositions include polyethylene glycol, for example, having at least 2, 3, 5, 10, or 100 repeating units. In other embodiments, the compositions are free or essentially free from polyethylene glycol, for example, polyethylene glycol having at least 2, 3, 10, or 100 repeating units. If present, the amount of polyethylene glycol may be from about 0.01 to about 10 wt. %, about 0.1 to about 5 wt. %, or about 0.1 to about 3 wt. %, including ranges and sub-ranges therebetween, based on the total weight of the compositions.

In various embodiments, the compositions of the instant disclosure are free or essentially free from anionic surfactants. In other embodiments, the compositions include one or more anionic surfactants. Anionic surfactants are known in the art. Nonlimiting examples include sulfate surfactants, isethionate surfactants, sarcosinate surfactants, sulfonate surfactants, taurate surfactants, etc. If present, the total amount of the one or more anionic surfactants may be from about 0.01 to about 5 wt. %, about 0.01 to about 3 wt. %, about 0.01 to about 1 wt. %, about 0.1 to about 4 wt. %, or about 0.1 to about 2 wt. %, based on the total weight of the hair treatment composition. In other embodiments, the compositions of the instant disclosure are free or essentially free from anionic surfactants.

In various embodiments, the hair treatment compositions of the instant disclosure are free or essentially free from anionic polymers. In other embodiments, however, the compositions include one or more anionic polymers. In the context of the present disclosure, the term "anionic polymers" is understood as meaning those polymers which carry in a protic solvent under standard conditions at least one structural unit having permanently anionic groups, the anionic groups having to be compensated by counterions while maintaining electroneutrality. As contemplated herein, anionic groups are, for example, carboxylate, sulfate, or sulfonate groups. Nonlimiting examples of anionic polymers include anionic polyurethanes, sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and combinations thereof.

In a preferred embodiment, the compositions of the instant disclosure are free or essentially free from anionic polymers. For example, the compositions may be free or essentially free from any one or more of the anionic polymers referenced above. In addition, the compositions of the instant disclosure may be free or essentially free from one or more, or all of the anionic polymers selected from anionic polyurethanes, sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and a combination thereof.

In various embodiments, the hair treatment compositions of the instant disclosure include one or more polyurethanes. However, in other embodiments, the hair treatment compositions are free or essentially free from polyurethanes.

FURTHER EMBODIMENTS

In various embodiments, the compositions of the instant disclosure include one or more silicones. In other embodiments, the compositions are preferably free or essentially free from silicones. Nonlimiting examples of silicones include dimethicone, dimethiconol, cyclomethicone, polysilicone-11, phenyl trimethicone, trimethylsilylamodimethicone, and stearoxytrimethylsilane. In a preferred embodiment, the one or more silicones are non-volatile silicone oils. Useful silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or 2-phenylethyl) trimethylsiloxysilicates. Other examples of silicone oils that may be mentioned include volatile linear or cyclic silicones, such as those with a viscosity 8 centistokes (8×106 $m^2/s$) and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or combinations thereof. In various embodiments, the hair treatment compositions include one or more silicone oils chosen from dimethicone, dimethiconol, cyclomethicone, polysilicone-11, phenyl trimethicone, and amodimethicone, and a combination thereof.

In various embodiments, the compositions of the instant disclosure may optionally include one or more of polyethylene glycols (PEG), anionic surfactants, nonionic surfactants, anionic polymers, silicones including amine functionalized silicones, or combinations thereof. In other embodiments, the compositions of the instant disclosure are free or essentially free from one or more of polyethylene glycols (PEG), nonionic surfactants, anionic surfactants, anionic polymers, silicones including amine functionalized silicones, or combinations thereof. In various embodiments, the hair treatment compositions are free or essentially free from silicones, including but not limited to amodimethicone, dimethicone, dimethiconol, anionic silicones, silicone elastomers, etc.

In certain embodiments, the compositions include polyethylene glycol, for example, having at least 2, 3, 5, 10, or 100 repeating units. In other embodiments, the compositions are free or essentially free from polyethylene glycol, for example, polyethylene glycol having at least 2, 3, 10, or 100 repeating units. If present, the amount of polyethylene glycol may be from about 0.01 to about 10 wt. %, about 0.1 to about 5 wt. %, or about 0.1 to about 3 wt. %, including ranges and sub-ranges therebetween, based on the total weight of the compositions.

In various embodiments, the compositions of the instant disclosure are free or essentially free from anionic surfactants. In other embodiments, the compositions include one or more anionic surfactants. Anionic surfactants are known in the art. Nonlimiting examples include sulfate surfactants, isethionate surfactants, sarcosinate surfactants, sulfonate surfactants, taurate surfactants, etc. If present, the total amount of the one or more anionic surfactants may be from about 0.01 to about 5 wt. %, about 0.01 to about 3 wt. %, about 0.01 to about 1 wt. %, about 0.1 to about 4 wt. %, or about 0.1 to about 2 wt. %, based on the total weight of the hair treatment composition. In other embodiments, the compositions of the instant disclosure are free or essentially free from anionic surfactants.

In various embodiments, the hair treatment compositions of the instant disclosure are free or essentially free from anionic polymers. In other embodiments, however, the compositions include one or more anionic polymers. In the context of the present disclosure, the term "anionic polymers" is understood as meaning those polymers which carry in a protic solvent under standard conditions at least one structural unit having permanently anionic groups, the anionic groups having to be compensated by counterions while maintaining electroneutrality. As contemplated herein, anionic groups are, for example, carboxylate, sulfate, or sulfonate groups. Nonlimiting examples of anionic polymers include anionic polyurethanes, sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and combinations thereof.

In a preferred embodiment, the compositions of the instant disclosure are free or essentially free from anionic polymers. For example, the compositions may be free or essentially free from any one or more of the anionic polymers referenced above. In addition, the compositions of the instant disclosure may be free or essentially free from one or more, or all of the anionic polymers selected from anionic polyurethanes, sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and a combination thereof.

In various embodiments, the hair treatment compositions include one or more amino functionalized silicones. In other embodiments, the compositions do not include one or more amino functionalized silicones, i.e., the compositions are free or essentially free from amino functionalized silicones. Nonlimiting examples of amino functionalized silicones include amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a combination thereof. Amodimethicone is a particularly useful amino functionalized silicone.

In various embodiments, the hair treatment compositions of the instant disclosure include one or more polyurethanes. However, in other embodiments, the hair treatment compositions are free or essentially free from polyurethanes.

PREFERRED EMBODIMENTS

In various embodiments, the essentially anhydrous hair treatment composition comprises, consists essentially of, or consists of:

(a) about 3 to about 30 wt. %, preferably about 5 to about 25 wt. %, more preferably about 5 to about 20 wt. % of one or more monoalcohols having from 2 to 8 carbon atoms, preferably wherein the one or more monoalcohols are selected from ethanol, propanol, butanol, pentanol, hexanol, isopropyl alcohol, cyclohexanol, isobutyl alcohol, 2-methyl-2-butanol (2-methylbutan-2-ol), or combinations thereof; wherein more preferably at least one of the one or more monoalcohols is ethanol;

(b) about 2 to about 15 wt. %, preferably about 3 to about 12 wt. %, more preferably about 3 to about 10 wt. % of one or more fatty alcohols, preferably wherein the one or more fatty alcohols are selected from $C_{10}$-$C_{30}$ fatty alcohols that are branched, straight, saturated, unsaturated, or combinations thereof, more preferably wherein the one or more fatty alcohols are selected from decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, oleyl alcohol, myricyl alcohol, or combinations thereof, even more preferably, wherein at least one of the one or more fatty alcohols is cetearyl alcohol;

wherein (a) is in an amount equal to or greater amount than (b), preferably wherein (a) and (b) are in a weight ratio of about 1:1 to about 10:1 ((a):(b)), more preferably wherein the weight ratio is about 1.5:1 to about 4:1 ((a):(b));

(c) about 50 to about 90 wt. %, preferably about 60 to about 88 wt. %, more preferably about 65 to about 82 wt. % of one or more fatty compounds other than fatty alcohols of (b), wherein preferably the one or more fatty compounds are selected from fatty esters, fatty ethers, propylene glycol fatty esters, fatty carbonates, silicone oils, or a combination thereof, more preferably wherein at least one of the one or more fatty compounds is a propylene glycol fatty ester, more preferably wherein the one or more fatty compounds is a propylene glycol fatty acid ester selected from propylene glycol monolaurate, propylene glycol ricinoleate, propylene glycol monooleate, propylene glycol monocaprylate, propylene glycol dicaprylate/dicaprate, propylene glycol dioctanoate, or a combination thereof;

(d) about 1 to about 12 wt. %, preferably about 1.5 to about 10 wt. %, more preferably about 2 to about 6 wt. % of one or more cationic surfactants, preferably wherein the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and combinations thereof, wherein more preferably at least one of the one or more cationic surfactants is an amidoamine surfactant;

wherein the composition is free or essentially free from propylene glycol;

optionally, wherein the composition is free or essentially free from ethylene glycol, propylene glycol, butylene glycol, hexylene glycol, pentylene glycol, diethylene glycol, dipropylene glycol, 1,3 propanediol, or a combination thereof; or wherein the compositions is free or essentially free from glycols having from 2 to 10 carbon atoms; and (e) optionally, about 0.01 to about 10 wt., preferably about 0.1 to about 8 wt. %, more preferably about 1 to about 5 wt. % of one or more miscellaneous ingredients, wherein preferably the one or more ingredients are selected from preservatives, fragrances, pH adjusters, salts, chelating agents, buffers, composition colorants, fillers (such as talc, calcium carbonate, silica, including hydrated silica), vitamins, botanical extracts, and a combination thereof. For example, the compositions may include silica (or hydrated silica), tocopherol, fragrances, or a combination thereof all percentages by weight are based on the total weight of the composition.

The hair treatment composition is preferably a solubilized, non-emulsified composition until contact with water, whereupon the composition forms a lamellar phase in situ. In further embodiments, the hair treatment composition is transparent or translucent.

In further embodiments, the essentially anhydrous hair treatment composition comprises, consists essentially of, or consists of:

(a) about 3 to about 30 wt. %, preferably about 5 to about 25 wt. %, more preferably about 5 to about 20 wt. % of ethanol;

(b) about 2 to about 15 wt. %, preferably about 3 to about 12 wt. %, more preferably about 3 to about 10 wt. % of one or more fatty alcohols, preferably wherein the one or more fatty alcohols are selected from $C_{10}$-$C_{30}$ fatty alcohols, more preferably wherein the one or more fatty alcohols are selected from decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, oleyl alcohol, myricyl alcohol, or combinations thereof, even more preferably, wherein at least one of the one or more fatty alcohols is cetearyl alcohol;

wherein (a) is in an amount equal to or greater amount than (b), preferably wherein (a) and (b) are in a weight ratio of about 1:1 to about 10:1 ((a):(b)), more preferably wherein the weight ratio is about 1.5:1 to about 4:1 ((a):(b));

(c) about 50 to about 90 wt. %, preferably about 60 to about 88 wt. %, more preferably about 65 to about 82 wt. % of one or more fatty compounds other than fatty alcohols of (b) selected from fatty esters, fatty ethers, propylene glycol fatty esters, fatty carbonates, silicone oils, or a combination thereof, more preferably wherein at least one of the one or more fatty compounds is a propylene glycol fatty esters selected from propylene glycol monolaurate, propylene glycol ricinoleate, propylene glycol monooleate, propylene glycol monocaprylate, propylene glycol dicaprylate/dicaprate, propylene glycol dioctanoate, or a combination thereof;

(d) about 1 to about 12 wt. %, preferably about 1.5 to about 10 wt. %, more preferably about 2 to about 6 wt. % of one or more amidoamine surfactants selected from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, stearamidoethyldiethylamine, or a combination thereof, preferably wherein the amidoamine surfactant is stearamidopropyl dimethylamine;

wherein the composition is free or essentially free from propylene glycol;

optionally, wherein the composition is free or essentially free from ethylene glycol, propylene glycol, butylene glycol, hexylene glycol, pentylene glycol, diethylene glycol, dipropylene glycol, 1,3 propanediol, or a combination thereof; or wherein the compositions is free or essentially free from glycols having from 2 to 10 carbon atoms; and (e) optionally, about 0.01 to about 10 wt., preferably about 0.1 to about 8 wt. %, more preferably about 1 to about 5 wt. % of one or more miscellaneous ingredients, wherein preferably the one or more miscellaneous ingredients are selected from preservatives, fragrances, pH adjusters, salts, chelating agents, buffers, composition colorants, fillers (such as talc, calcium carbonate, silica, including hydrated silica), vitamins, botanical extracts, and a combination thereof. For example, the compositions may include silica (or hydrated silica), tocopherol, fragrances, or a combination thereof;

all percentages by weight are based on the total weight of the composition.

The hair treatment composition is preferably a solubilized, non-emulsified composition until applied to the wet or damp hair, whereupon the composition forms a lamellar phase in situ. In further embodiments, the hair treatment composition is transparent or translucent.

Methods

The hair treatment compositions of the instant disclosure are useful for treating the hair, for example, for conditioning, managing, and improving the look and feel of hair. In various embodiments, the hair treatment composition is a solubilized, non-emulsified composition. In further embodiments, the composition is a solubilized, non-emulsified composition, whereupon contact with water the composition forms an opaque appearance in situ. In other embodiments, the composition is a solubilized, non-emulsified composition, whereupon contact with water the composition forms a lamellar phase in situ. A "lamellar phase" refers generally to packing of polar-headed long chain nonpolar-tail molecules in an environment of bulk polar liquid (i.e., water from the hair), as sheets of bilayers separated by bulk liquid. The compositions can be applied to the wet or damp hair or diluted with water then applied to hair and may be massaged into the hair, for example, with the hands, and/or spread throughout the hair with a comb or brush. This results in a smoothing and softening of the hair, which reduces frizz, dryness, and unwanted volume. The compositions can remain in the hair or can optionally be rinsed from the hair prior to drying and/or styling of the hair. Preferably, the hair treatment compositions are rinsed from the hair after being applied and massaged into the hair.

The hair treatment compositions, in certain embodiments, may be used as a leave-on product. The hair treatment compositions are applied to wet or damp hair or diluted with water then applied to hair and allowed to remain on the hair indefinitely, i.e., the hair composition is not removed or rinsed from the hair prior to drying or styling the hair.

The methods of treating hair according to the disclosure also include methods according to various routines. For instance, the compositions may be mixed with a shampoo (or conditioner) prior to application to the hair. Alternatively, the composition may be layered on top of (or lathered into) hair to which the shampoo (or conditioner) is already applied. Furthermore, the composition may be applied separate from the shampoo (or conditioner), i.e., applied to the hair after the shampoo (or conditioner) has been rinsed from the hair. In some instances, it is preferable to treat the hair with a composition of the instant disclosure prior to shampooing the hair, e.g., apply the composition to wet or damp hair prior to application of a shampoo to the hair. The hair may additionally (optionally) be treated with a conditioner after shampooing.

Kits

The hair compositions of the instant disclosure may be incorporated into a kit. For example, the kits may include at least one hair treatment composition according to the instant disclosure and one or more additional compositions, for example, a shampoo, a conditioner, etc. The various compositions are separately contained in the kits. In some instances, the kits include one or more compositions according to the instant disclosure and a shampoo, both of which are separately contained. The kits may also include one or more compositions according to the instant disclosure, a shampoo, and a conditioner, all of which are separately contained. Instructions, mixing components, brushes, gloves, measuring tools, etc., may optionally be included in the kits.

The compositions may be packaged in a variety of different containers, such as, for example, a ready-to-use container. Non-limiting examples of useful packaging include tubes, jars, caps, unit dose packages, and bottles, including squeezable tubes and bottles. In some cases, the packaging is a tube, such as a tube with two compartments, or dual tubes, each forming a separate compartment. Each compartment may include a different composition. For example, one tube or compartment may include a composition according to the instant disclosure, and the other tube may include a composition to be used with the composition, for example, a shampoo, a conditioner, an all-in-one shampoo/conditioner (i.e., a conditioning shampoo; also referred to as a "co-wash").

In various embodiments, the hair compositions of the instant disclosure are packaged as a spray product, which allows a user to apply the compositions to hair by spraying the composition onto the hair. Furthermore, the compositions may be packaged in a spray bottle, which can be a pump spray bottle that is manually actuated, or the spray bottle can be pressurized such that the compositions are dispensed from a pressurized aerosol container. A propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

Methods of treating hair according to the disclosure will vary but typically include applying a hair treatment composition of the instant disclosure to wet or damp hair or diluting the composition with water then applying to hair, allowing the composition to remain on the hair for a sufficient amount of time, and rinsing the compositions from the hair. The composition may be applied to the hair in a sequence with other compositions. For example, the compositions may be applied to the hair before shampooing the hair, after shampooing the hair, before conditioning the hair, and/or after conditioning the hair. The compositions, however, are not required to be used in a sequence.

The compositions of the instant disclosure may be allowed to remain on the hair for a minimum amount of time before being rinsed from the hair, but it is not necessary to allow the composition to remain on the hair. Conveniently, the compositions can be applied and allowed to remain on the hair for a period of time that is typical for regular shampooing and/or conditioning. For example, the composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

The hair treatment composition may be applied to the hair immediately after or before the hair it treated with another composition (e.g., a shampoo and/or a conditioner). For example, the hair-treatment compositions may be applied to the hair within about 1, 2, 5, 10, or 20 minutes before or after a shampoo and/or a conditioner is applied to the hair.

The compositions of the instant disclosure are unique in their ability to provide hair with improved manageability, frizz control, and smoothness. Accordingly, the instant disclosure relates to methods for treating hair, for example, for improving the manageability of hair, for imparting frizz control, and for adding smoothness. More specifically, the compositions may be used in methods for conditioning the hair, providing curl definition to the hair, providing frizz control to the hair, improving ease of combability and detangling, and providing smoothness.

Additional Cationic Surfactants

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3) oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and combinations thereof.

In some cases, it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include those corresponding to the general formula (I) below:

(I)

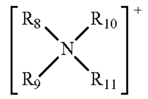

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula (II) below:

(II)

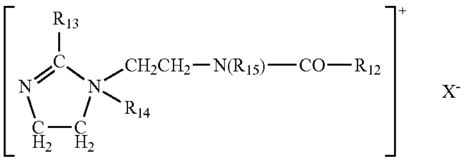

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a combination of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name "REWOQUAT W 75" by the company, Rewo;

C. a quaternary diammonium or triammonium salt, in particular of formula (V):

(III)

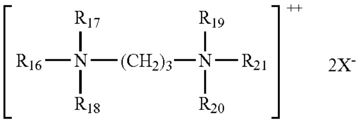

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N—(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, "Finquat CT-P," sold by the company, Finetex (Quaternium 89), and "Finquat CT," sold by the company, Finetex (Quaternium 75), D. Cationic/cationizable surfactants, for example of the general structure

R4-A-R5-B wherein R4 is a saturated or unsaturated, straight or branched alkyl chain with 8 to 24 C atoms, R5 is a straight or branched alkyl chain with 1 to 4 C atoms, A is selected from:

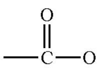 and

-continued

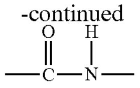

and and B is selected from

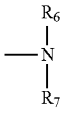

wherein $R_6$ and $R_7$ are the same or different is H or an alkyl chain with 1 to 4 C atoms, hydroxyl alkyl chain with 1 to 4 C atoms and dihydroxyl alkyl chain with 2 to 4 C atoms,

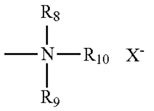

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24 C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl butylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl butylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines, preferably, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and combinations thereof. In various embodiments, it is preferably that at least one of the one or more cationic surfactants is a fatty dialkylamine.

Fatty dialkylamines include fatty amidoamine compounds, their salts, and combinations thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine. In a preferred embodiment, the compositions of the instant disclosure include stearamidopropyl dimethylamine, and optionally one or more additional cationic surfactants Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and combinations thereof. In particular, lactic acid or tartaric acid or combinations thereof are useful, especially in combination with fatty dimethylamines such as, for example, stearamidopropyl dimethylamine.

EXAMPLES

Various changes can be made in the above-described compositions and methods without departing from the scope of the invention. Accordingly, it is intended that all disclosure contained in the above description and in the examples given below, shall be interpreted as illustrative and not in a limiting sense.

Example 1
(Compositions)

| | | | | Comparative | |
|---|---|---|---|---|---|
| | | | A | B | C |
| (a) | Ethanol | ETHANOL | 10 | 20 | 4.5 |
| (b) | Fatty Alcohol | CETYL ALCOHOL AND/OR OLEYL ALCOHOL | 5 | 1.5 | 4.7 |
| Weight Ratio of (a):(b) | | | 2:1 | 13.3:1 | 0.96:1 |
| (c) | Cationic Surfactant | STEARAMIDOPROPYL DIMETHYLAMINE | 2.8 | 1.2 | 4.3 |
| (d) | Fatty Compound | PROPYLENE GLYCOL DICAPRYLATE/DICAPRATE | 82.2 | 0.5 | |
| | | DICAPRYLYL ETHER | | 0.5 | |
| | | DICAPRYLYL CARBONATE | | 0.9 | |
| | | DIETHYLHEXYL MALEATE | | | 86 |
| | Glycol | PROPYLENE GLYCOL | | 74.4 | |
| (e) | Miscellaneous | pH adjusters, salts, fragrances, preservatives, antioxidants, chelating agents, compositions colorants, botanical extracts, etc. | ≤5 | ≤5 | ≤5 |
| Stable[1] | | | Yes | Yes | No |

[1]Stored at 4° C. for 3 days, then maintained at room temperature for 5 hours.

Example 2

(Cosmetic Properties)

Testing was carried out to determine how the compositions of Example 1 performed. SA 20 bleached Caucasian hair swatches curl type 3A-3B (Andre Walker curling system) were obtained and initially washed with a standard shampoo. After rinsing, one swatch was set aside for use as a control. The control swatch was simply hung to dry after cleansing with the standard shampoo. After rinsing the shampoo from the remaining hair swatches, the compositions of Example 1 were individually applied to the damp hair swatches in an amount of 1 gram of composition per 1 gram of hair. Inventive Compositions A and Comparative Composition C were diluted with water (up to 10×) and massaged into the hair swatches and then allowed to remain on the hair for 10 minutes. After 10 minutes, the Inventive Composition A and Comparative Composition C were rinsed from the hair swatches and the hair swatches were hung to dry. Comparative Composition B was applied to a damp hair swatch and massaged into the hair swatch. However, Comparative Composition B was not allowed to remain on the hair for 10 minutes. Instead, it was immediately rinsed from the hair swatch, and the hair swatch was hung to dry. After all hair swatches were dry, they were visually examined to determined softness, smoothness, alignment, and frizz control (lack of frizz). The hair swatch treated with Inventive Composition A was soft and smooth similar to the hair treated with Comparative Compositions B and C. Furthermore, the hair swatch treated with Inventive Composition A exhibited the best fiber alignment and frizz control (lack of frizz). All compositions performed better than the control. Images of the hair swatches are provided in The FIGURE.

Example 3

(Stability)

Stability testing was carried out on the compositions of Example 1. The compositions were separately placed in sealed transparent glass containers and maintained at a temperature of 4° C. for 3 days. After 3 days, the glass containers containing the compositions were maintained at room temperature (about 25° C.) for 5 hours to provide sufficient time for the compositions to heat to room temperature. After 5 hours, the glass containers were visually evaluated for phase separation. Inventive Composition A and Comparative Composition B appeared clear (transparent) and homogenous, without any signs of phase separation or sedimentation. Comparative Composition C, however, was not homogeneous. The composition was cloudy, and crystalline-like sedimentation formed on the bottom of the glass container. Without wishing to be bound by any particular theory, the inventors believe the sedimentation is the crystallization of amidoamine (stearamidopropyl dimethylamine)

The terms "comprising," "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

A "composition colorant" is a compound or ingredient that colors the composition but does not have an appreciable coloring effect on hair. In other words, the composition colorant is included to provide a color to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair. Thus, a composition colorant is different from a hair coloring agent. A composition colorant colors the compositions; a "hair coloring agent," on the other hand may change the color of the compositions (and often does) but also changes the color of hair The term "rinse-off" as used herein indicates that the composition is used in a context whereby the composition is ultimately rinsed or washed from the treated surface, (e.g. skin, hair, or hard surfaces) either after or during the application of the product. These rinse-off compositions are to be distinguished from compositions referred to a "leave-on" compositions. For example, a rinse-off composition is applied to the hair, optionally allowed to remain on the hair for a short time (e.g., a few second up to about 5, 10, or 15 minutes) and subsequently rinsed from the hair before the hair styled.

The compositions described throughout this disclosure may be a "leave-on" composition. A "leave-on" (also called "leave-in") composition refers to a composition that is applied to skin or hair and is not subjected to immediate rinsing and/or washing, for example for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

A "lamellar phase" refers generally to packing of polar-headed long chain nonpolar-tail molecules in an environment of bulk polar liquid (i.e., water from the hair), as sheets of bilayers separated by bulk liquid.

The term "non-linear fatty acids" as used in the instant disclosure refers to unsaturated fatty acid and/or branched fatty acids.

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure. A human can typically see through a transparent composition, for example, and read the text on the other side of a clear glass or clear plastic bottle containing the composition.

The term "translucent" with respect to a translucent composition indicates that the composition has a transmittance of at least 50% at a wavelength of 600 nm, for example measured using a Lambda 40 UV-visible spectrometer. A human cannot likely see through a translucent composition, for example, and read the text on the other side of a clear glass or clear plastic bottle containing the composition. Rather, the text is usually blurred and difficult or not possible to read, yet movement and structure can normally be identified.

The term "opaque" with respect to an opaque composition indicates that the composition is not transparent or translucent, i.e., has a transmittance of less than 50% at a wavelength of 600 nm, for example measured using a Lambda 40 UV-visible spectrometer.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the composition. Nonetheless, the compositions may include less than about 2 wt. %, less than about 1 wt. %, less than about 0.5 wt. %, less than about 0.1 wt. %, less than 0.01 wt. %, or none of the specified material. For instance, the compositions of the instant disclosure are "essentially anhydrous." Therefore, the composition includes less than about 5 wt. % of water. Nonetheless, the compositions may include less than about 2 wt. %, less than about 1 wt. %, less than about 0.5 wt. %, less than about 0.1 wt. %, less than 0.01 wt. %, or no water.

The term "active material" as used herein with respect to the percent amount of an ingredient or raw material, refers to 100% activity of the ingredient or raw material. All ingredients are listed as 100% active material unless otherwise indicated.

"Cosmetically acceptable" means that the item in question is compatible with a keratinous substrate such as skin and hair. For example, a "cosmetically acceptable carrier" means a carrier that is compatible with a keratinous substrate such as skin and hair.

Throughout the disclosure, the term "a combination thereof" (or a mixture thereof) may be used following a list of elements as shown in the following example where letters A-F represent the elements: "one or more elements selected from A, B, C, D, E, F, or a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is like the phrase "one or more elements selected from A, B, C, D, E, F, and a combination of any two or more of A, B, C, D, E, and F."

Likewise, the term "a salt thereof" also relates to "salts thereof." Thus, where the disclosure refers to "an element selected from A, B, C, D, E, F, a salt thereof, or a combination thereof," it indicates that that one or more of A, B, C, D, and F may be included, one or more of a salt of A, a salt of B, a salt of C, a salt of D, a salt of E, and a salt of F may be included, or a combination of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

Some of the compounds discussed throughout the disclosure may be in the form of a salt in the composition or added to the composition in the form of a salt (and dissociate in the composition). Thus, all compounds and amounts of compounds relate to both the salt form of the compound and to the disassociated form of the compound. In other words, even if the expression "a salt thereof" is not specifically or expressly stated with respect to ingredients that can form salts or are available as salts, it is understood that the salt form of the compound is included.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions of the instant disclosure can be free or essentially free of any components and elements positively recited throughout the instant disclosure.

Some of the various categories of components identified may overlap. In such cases where overlap may exist and the composition includes both components (or the composition includes more than two components that overlap), an overlapping component or ingredient does not represent more than one component of the claims. For example, if a polyacrylate falls within the description of a thickening polymer and within the description of film forming polymer, a single polyacrylate is understood as being only the thickening polymer or only the film forming polymer. A single polyacrylate cannot simultaneously be construed as both a thickening polymer and a film forming polymer, for example, when the claims set forth both a thickening polymer and a film forming polymer (even though the polyacrylate may function as both a thickening polymer and a film forming polymer). In other words, a single compound or ingredient cannot simultaneously serve as two different components or elements of a claim.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. An essentially anhydrous hair treatment composition comprising:

(a) about 3 to about 18 wt. % of one or more linear or branched monoalcohols selected from ethanol, propanol, butanol, pentanol, hexanol, isopropyl alcohol, isobutyl alcohol, and 2-methyl-2-butanol;

(b) about 2 to about 15 wt. % of one or more fatty alcohols;

wherein (a) is in an amount equal to or greater than (b);

(c) about 50 to about 90 wt. % of one or more fatty compounds selected from fatty esters and fatty ethers; and (d) about 1 to about 12 wt. % of one or more cationic surfactants;

wherein the composition is essentially free from glycols having from 2 to 10 carbon atoms and glycerin; and wherein the composition comprises less than about 5 wt. % of C6-C16 alkanes and linear or branched hydrocarbons composed of only carbon and hydrogen atoms with more than 16 carbon atoms; and all percentages by weight are based on a total weight of the composition.

2. The composition of claim 1, wherein the one or more linear or branched monoalcohols comprises ethanol.

3. The composition of claim 1, wherein the composition is a solubilized, non-emulsified composition until contact with water, whereupon the composition forms a lamellar phase in situ.

4. The composition of claim 1, wherein the one or more fatty alcohols are selected from $C_{10}$-$C_{30}$ fatty alcohols that are branched, straight, saturated, or unsaturated.

5. The composition of claim 1, wherein the one or more fatty alcohols are selected from decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, oleyl alcohol, and myricyl alcohol.

6. The composition of claim 1, wherein the one or more fatty compounds comprise one or more fatty esters selected from propylene glycol monolaurate, propylene glycol ricinoleate, propylene glycol monooleate, propylene glycol monocaprylate, propylene glycol dicaprylate/dicaprate, and propylene glycol dioctanoate.

7. The composition of claim 1, wherein the composition is transparent.

8. The composition of claim 1, wherein the one or more cationic surfactants are selected from amidoamine surfactants.

9. The composition of claim 8, wherein the amidoamine surfactants are selected from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamidopropyl dimethylamine, cocamidopropyl dimethylamine, tallamidopropyl dimethylamine, brassicamidopropyl dimethylamine, olivamidopropyl dimethylamine, and combinations thereof.

10. A method for conditioning, managing, and improving the look and feel of hair comprising applying the hair treatment composition of claim 1 to the hair.

11. The method of claim 10, further comprising rinsing the hair treatment composition from the hair.

* * * * *